(12) United States Patent
Saltzman et al.

(10) Patent No.: US 11,766,400 B2
(45) Date of Patent: Sep. 26, 2023

(54) BIODEGRADABLE CONTRACEPTIVE IMPLANTS

(71) Applicants: Yale University, New Haven, CT (US); Family Health International, Durham, NC (US)

(72) Inventors: W. Mark Saltzman, New Haven, CT (US); Elias Quijano, Durham, CT (US); Fan Yang, Branford, CT (US); Zhaozhong Jiang, New Haven, CT (US); Derek Owen, Durham, NC (US)

(73) Assignees: YALE UNIVERSITY, New Haven, CT (US); FAMILY HEALTH INTERNATIONAL, Durham, NC (US)

(*) Notice: Subject to any disclaimer, the term of this patent is extended or adjusted under 35 U.S.C. 154(b) by 0 days.

(21) Appl. No.: 16/344,663

(22) PCT Filed: Oct. 24, 2017

(86) PCT No.: PCT/US2017/058107
§ 371 (c)(1),
(2) Date: Apr. 24, 2019

(87) PCT Pub. No.: WO2018/081138
PCT Pub. Date: May 3, 2018

(65) Prior Publication Data
US 2020/0054553 A1 Feb. 20, 2020

Related U.S. Application Data

(60) Provisional application No. 62/411,872, filed on Oct. 24, 2016.

(51) Int. Cl.
*A61K 9/00* (2006.01)
*A61K 31/567* (2006.01)

(52) U.S. Cl.
CPC .......... *A61K 9/0024* (2013.01); *A61K 31/567* (2013.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 6,140,081 A | 10/2000 | Barbas | |
| 6,453,242 B1 | 9/2002 | Eisenberg | |
| 6,534,261 B1 | 3/2003 | Cox | |
| 6,610,512 B1 | 8/2003 | Barbas | |
| 6,746,838 B1 | 6/2004 | Choo | |
| 6,866,997 B1 | 3/2005 | Choo | |
| 7,067,617 B2 | 6/2006 | Barbas | |
| 2002/0165356 A1 | 11/2002 | Barbas | |
| 2003/0021591 A1 | 1/2003 | Grosvenor | |
| 2004/0054372 A1* | 3/2004 | Corden | A61L 27/44 606/77 |
| 2004/0197892 A1 | 10/2004 | Moore | |
| 2005/0147962 A1 | 7/2005 | Wagstrom | |
| 2007/0154989 A1 | 7/2007 | Barbas | |
| 2007/0213269 A1 | 9/2007 | Barbas | |
| 2009/0130176 A1* | 5/2009 | Bossy-Nobs | A61F 2/16 424/428 |
| 2015/0150987 A1* | 6/2015 | Gaudriault | A61K 31/7048 514/20.5 |

FOREIGN PATENT DOCUMENTS

| | | |
|---|---|---|
| CN | 106119269 | 11/2016 |
| WO | 9853059 | 11/1998 |
| WO | 2003016496 | 2/2003 |
| WO | WO2009036999 | * 3/2009 |
| WO | 2013176772 | 11/2013 |
| WO | 2014018423 | 6/2014 |
| WO | 2017089567 | 6/2017 |
| WO | 2017089570 | 6/2017 |
| WO | 2017189870 | 11/2017 |
| WO | 2017189914 | 11/2017 |

OTHER PUBLICATIONS

Jadelle Prescribing Information, Revised Dec. 2016 (Year: 2016).*
Ma et al., A biodegradable levonorgestrel-releasing implant made of PCL/F68 compound as tested in rats and dogs, Contraception 74 (2006) 141-147 (Year: 2006).*
Alaee, et al., "Preparation of a reservoir type levonorgestrel delivery system using high molecular weight poly L-Lactide", Iruan J Pharmaceutical Res., 8(2):8-93 (2009).
Benson, et al., DNA rendering of polyhedral meshes at the nanoscale, Nature, 523:441-4 (2015).
Braasch, et al., "Locked nucleic acid (LNA): fine-tuning the recognition of DNA and RNA", Chem. Biol., 8:1-7 (2001).
Brown, et al., "An easy-to-prepare mini-scaffold for DNA origami", Nanoscale, 7:16621-4 (2015).
Chasteen, et al., "Eliminating helper phage from phage display", Nucleic Acids Res., 34(21):e145 (2006).
Cherny, et al., "DNA unwinding upon strand-displacement binding of a thymine-substituted polyamide to double-stranded DNA", Science, 254:1497-1500 (1993).
Cong, "Multiplex genome engineering using CRISPR/Cas systems", Science, 15:339(6121):819-23 (2013).
Dietz, et al., "Folding DNA into twisted and curved nanoscale shapes", Science, 325:725-30 (2009).

(Continued)

*Primary Examiner* — Jennifer A Berrios
(74) *Attorney, Agent, or Firm* — PABST PATENT GROUP LLP

(57) ABSTRACT

Biodegradable contraceptive implants and methods of making and using thereof, are preferably formed of poly(ω-pentadecalactone-co-p-dioxanone) [poly(PDL-co-DO)], a family of polyester copolymers that degrade slowly in the presence of water. The material is suitable as the basis of a biodegradable contraceptive implant that provides sustained release of a progestin at a rate similar to a commercially available nondegradable implant. In a preferred embodiment, the progestin is levonorgestrel (LNG), a hormone that prevents pregnancy by preventing the release of an egg from the ovary or by preventing fertilization of the egg by sperm. The implant may be inserted subcutaneously, allowing degradation over a period of up to about 18 or 24 months, eliminating the need for removal by a trained practitioner.

17 Claims, 9 Drawing Sheets

(56) References Cited

OTHER PUBLICATIONS

Douglas, et al., "Self-assembly of DNA into nanoscale three-dimensional shapes", Nature, 459:414-8 (2009).
Du, et al., "Multigene expression in vivo: supremacy of large versus small terminators for T7 RNA polymerase", Biotechnol Bioeng., 109(4):1043-50 (2012).
Elbaz, et al., "Genetic encoding of DNA nanostructures and their self-assembly in living bacteria", Nat. Commun., 7:11179 (2016).
Geary, et al., "RNA nanostructures. A single-stranded architecture for cotranscriptional folding of RNA nanostructures", Science, 345:799-804 (2014).
Govan, et al., "Stabilization and photochemical regulation of antisense agents through PEGylation", Bioconjug Chem., 22(10) 2136-42 (2011).
Han, et al., "Single-stranded DNA and RNA origami", Science, 358(6369) (2017).
Jiang, et al., "Lipase-catalyzed ciopolumerization of w-Pentadecalactone with p-Dioxanone and characterization of copolymer thermal and crystalline properties", Biomacromolecules, 8:2262-9 (2007).
Jinek, et al., "A programmable dual-RNA-guided DNA endonuclease in adaptive bacterial immunity", Science, 337(6096):816-21 (2012).
Ke, et al., "Three-dimensional structures self-assembled from DNA bricks", Science, 338:1177-83 (2012).
Kick, et al., "Efficient Production of Single-Stranded Phage DNA as Scaffolds for DNA Origami", Nano Lett., 15, 4672-6 (2015).
Kitchell, et al., "Preparation of biodegradable levonorgestrels rods", Long-Acting Contraceptive Delivery Systems, edited by Gerald I. Zatuchni, Harper and Row (1984).
Kim, et al., "Insertion and Deletion of Mutants of Fokl Restriction Endonuclease", J. Biol. Chem., 269(50):31978-31982 (1994b).
Kim, et al., "Chimeric restriction endonuclease", PNAS.,91:883-7 (1994a).
Kurreck, et al., "Design of antisense oligonucleotides stabilized by locked nucleic acids", Nucleic Acids Res., 30:1911-18 (2002).
Li, et al., "Alteration of the cleavage distance of Fok I restriction endonuclease by insertion mutagenesis", PNAS, 90:2764-2768 (1993).
Li, et al., "Functional domains in Fok I restriction endonuclease", PNAS, 89:4275-9 (1992).
Liu, et al., "Crystalline two-dimensional DNA-origami arrays", Angew Chem. Int. Ed., 50:264-7 (2011a).
Liu, et al., "Biodrgadation, biocompatibility and drug delivery in poly (w-pentadecalactone-co-p-dioxanone) corpolyesters", Biomaterial, 32:6646-54 (2011b).
Marchi, et al., "Toward larger DNA origami", Nano Lett., 14:5740-7 (2014).
Nafisi, et al., "Construction of a novel phagemid to produce custom DNA origami scaffolds", Synthetic Biology, 3(1):ysy015 (8 pages) (2018).
Nickels, et al., "DNA origami structures directly assembled from intact bacteriophages", Small, 10:1765-9 (2014).
Praetorius, et al., "Biotechnological mass production of DNA origami", Nature, 552(7683):84-87 (2017).
Rothemund, et al., "Algorithmic Self-Assembly of DNA Sierpinski Triangles", PLoS Biol., 2:2041-53 (2004).
Rothemund, "Folding DNA to create nanoscale shapes and patterns", Nature, 440:297-302 (2006).
Said, et al., "M1.3—a small scaffold for DNA Origami", Nanoscale, 5(1):284-90 (2013).
Sharma, et al., "Control of self-assembly of DNA tubules through integration of gold nanoparticles", Science, 323:112-6 (2009).
Shepherd, et al., "De novo design and synthesis of a 30-cistron translation-factor module", Nucleic Acids Res., 45(18):10895-905 (2017).
Shih, et al., "A 1.7-kilobase single-stranded DNA that folds into a nanoscale octahedron", Nature, 427(6975):618-21 (2004).
Torring, et al., "DNA origami: a quantum leap for self-assembly of complex structures", Chem. Soc. Rev., 40:5636-46 (2011).
Venziano, et al., "Designer nanoscale DNA assemblies programmed from the top down", Science, 352(6293):1534 (2016).
Wahlestedt, et al., "Potent and nontoxic antisense oligonucleotides containing locked nucleic acids", PNAS, 97(10)5633-8 (2000).
Winfree, et al., "Design and self-assembly of two-dimensional DNA crystals", Nature, 394(6693):539-44 (1998).
Wise, et al., "Long-term controlled delivery of leconorgestrel in rats by means of small biodegradable cylinders", J. Pharmmacol., 32:399-403 (1980).
Woo, et al., "Programmable molecular recognition based on the geometry of DNA nanostructures", Nat. Chem., 3(8):620-7 (2011).
Yan, et al., "DNA-templated self-assembly of protein arrays and highly conductive nanowires", Science, 301:1882-4 (2003).
Ye, et al., "Dual-controlled drug delivery across biodegradable copolymer. II. Delivery kinetics of levonorgestrel and estradiol from (matrix/matrix) laminate drug delivery system", J. of Controlled Release, 41:259-269 (1996).
Zhang, et al., "Complex wireframe DNA origami nanostructures with multi-arm junction vertices", Nat. Nanotechnol., 10(9):779-84 (2015).
Zhao, et al., "Organizing DNA origami tiles into larger structures using preformed scaffold frames", Nano Lett., 11:2997-3002 (2011).
International Search Report for corresponding PCT application PCT/US2017/058107 dated Jan. 8, 2018.

* cited by examiner

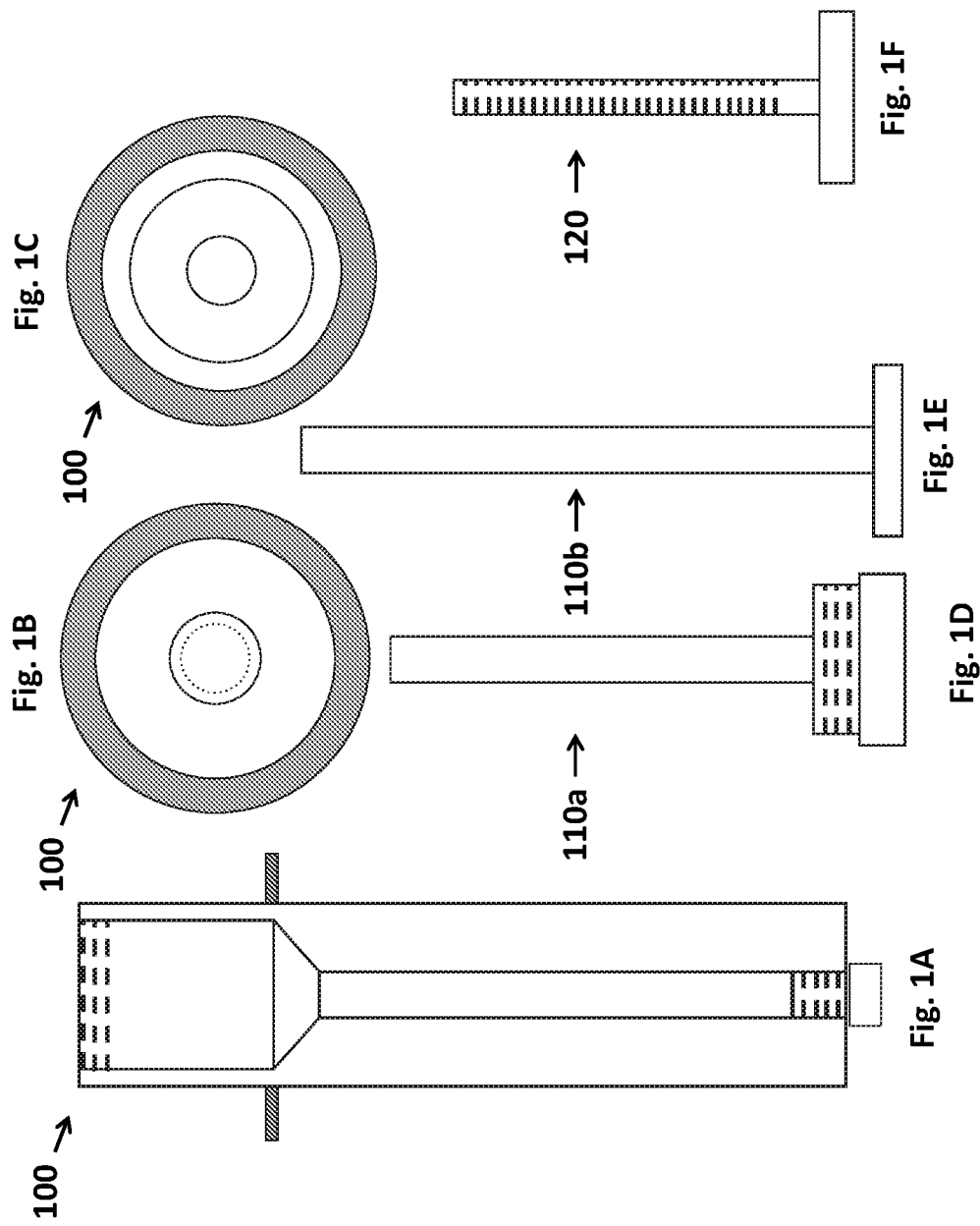

200a

200a

200b

200a

200b

200b

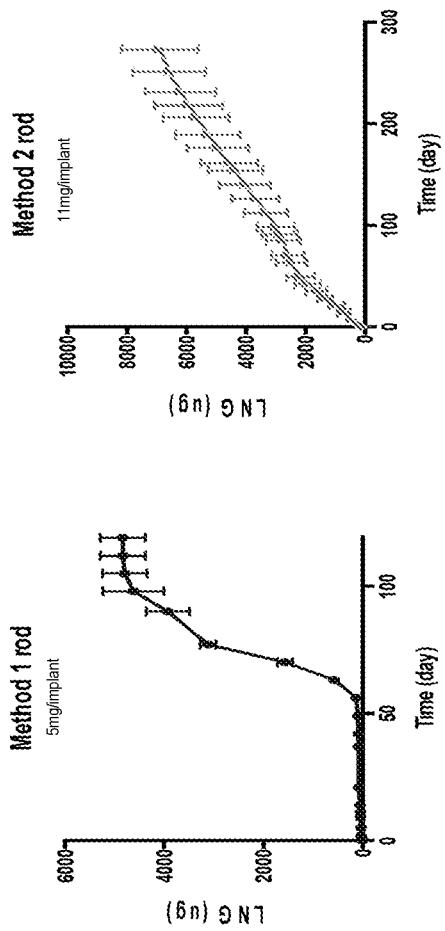
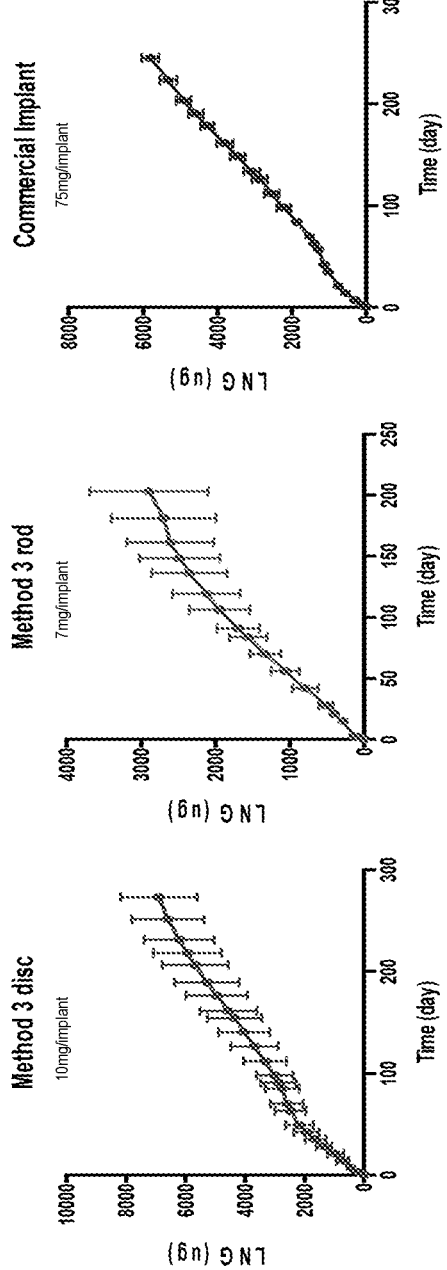

BIODEGRADABLE CONTRACEPTIVE IMPLANTS

CROSS-REFERENCE TO RELATED APPLICATIONS

This application is a National Phase application under 35 U.S.C. 371 of PCT/US2017/058107, filed Oct. 24, 2017, which claims benefit of U.S. Provisional Application No. 62/411,872, filed Oct. 24, 2016, and which are hereby incorporated herein by reference in their entirety.

STATEMENT REGARDING FEDERALLY SPONSORED RESEARCH

This invention was made with government support under AID-OAA-A-10-0060 awarded by the United States Agency for International Development. The government has certain rights in the invention.

FIELD OF THE INVENTION

This invention is in the field of contraceptive implants, specifically biodegradable contraceptive implants.

BACKGROUND OF THE INVENTION

There are a wide variety of methods available for preventing pregnancy. The most effective methods of birth control are achieved by means of vasectomy in males and tubal ligation in females, or removal of the reproductive organs. However, both of these procedures result in permanent sterility, and are thus undesirable for individuals who may wish to have children at a later time.

Not all contraceptive methods are appropriate for all situations. The most appropriate method of birth control depends on a woman's overall health, age, frequency of sexual activity, number of sexual partners, risk of venereal disease, desire to have children in the future, and family history of certain diseases.

Barrier devices such as diaphragms and cervical caps can be effective, but they have to be inserted correctly before each sexual interaction and they have to be used in conjunction with spermicide. Moreover, they are custom fitted, and thus, women have to be measured again after giving birth, after having pelvic surgery, or after gaining or losing more than 15 pounds.

Hormonal methods prevent pregnancy by regulating or stopping ovulation; thickening cervical mucus to block sperm from reaching the egg; or by thinning the lining of the uterus. Hormones can be introduced into the body through various methods, including pills, injections, skin patches, transdermal gels, vaginal rings, intrauterine systems, and implantable rods.

Intrauterine devices (IUDs) are small T-shaped devices that are inserted into the uterus and function effectively for many years at a time. Copper IUDs release small amounts of copper ions into uterine fluids and cervical mucus and inflammation induced by its presence, creating a toxic environment for sperm. Should fertilization still occur, implantation of the fertilized egg is usually prevented by the mere presence of the device, as well as by the inflammation induced by its presence. Hormonal IUDs release a progestin hormone into the uterus, which in addition to thickening the cervical mucus, inhibiting interaction between sperm and egg, and thinning the uterine lining, may also prevent the ovaries from releasing eggs.

Despite the availability of various contraceptive methods and devices, the need still exists for effective, long-term birth control options requiring minimal medical guidance. This is particularly true in those areas of the world where the medical infrastructure is poor, and where there is little access to doctors or nurse practitioners who can assist in family planning. While several platforms for the delivery of contraceptive hormones exist, distribution and use of these platforms present significant challenges under these conditions.

The use of oral contraceptives, for instance, requires regular access to monthly prescriptions, daily administration, and daily storage in stable conditions. IUDs and non-degradable, elastomer based implants, while not requiring daily administration, require access to trained medical specialists for initial insertion of the device, as well as for subsequent removal by a physician to restore fertility.

Thus, despite the availability of implantable contraceptive devices, there remains a need for contraceptive implants that are biodegradable, eliminating the need for removal.

It is therefore an object of the present invention to provide an implantable contraceptive delivery system that passively administers therapeutic doses of a contraceptive agent such as a progestin or a non-contraceptive active agent.

It is a further object of the invention to provide an implantable contraceptive delivery system that is biodegradable.

It is a further object of the invention to provide methods of inserting the implantable contraceptive delivery system.

It is a further object of the invention to provide methods of making the implantable contraceptive delivery system.

SUMMARY OF THE INVENTION

Biodegradable polymeric implants and methods of making and using thereof, are provided herein. In a preferred embodiment, the implant has a biocompatible polyester copolymer composition encapsulating a prophylactic agent of contraceptive nature. In the most preferred embodiment, the polyester is a poly(ω-pentadecalactone-co-p-dioxanone) [poly(PDL-co-DO)], a family of degradable polyester copolymers that degrade slowly in the presence of water. The material is semi-crystalline over all copolymer compositions, suitable for controlled delivery of molecules, retention of mechanical properties during degradation, and biocompatible. Hence, the material is suitable as the basis of a biodegradable contraceptive implant that provides sustained release of a progestin at a rate similar to a commercially available nondegradable implant, as well as has desirable mechanical and processing characteristics.

In a preferred embodiment, the progestin is levonorgestrel (LNG). LNG prevents pregnancy by preventing the release of an egg from the ovary or by preventing fertilization of the egg by sperm. LNG may also function by changing the lining of the uterus, thus preventing implantation of a fertilized egg.

The period during which the device is removable might be the same or different then the period of release. In some embodiments, product can be removable for a period equal to the period of efficacy minus about six months. In preferred embodiments, the implant degrades within about six month after the period of efficacy. For example, in some embodiments, drug (e.g., LNG) release occurs over a period of preferably 12-18 months, but implant degradation occurs over a period of 18 to 36 months. In other embodiments, the implant can be removable for up to a year or up to 18 months, with 18 months or 24 months of efficacy. In a particular embodiment, the implant is removable for up to a year with 18 months of efficacy. In this context, removable or removability means the implant retain sufficient mechanical properties to be removed (e.g., before or after release is complete), typically using forceps to physically withdraw the implant from under the skin. In some embodiments, degradation is complete within 6 months of the end of release.

The preferred polymer has intermediate amounts of the co-polymer (i.e. the % DO is 39-50%). The range of drug loading can be, for example, about 5% to about 30%, or higher, with approximately 25 weight % providing a preferred release. The implants are mechanically strong after incubation for nearly one year in buffered saline solutions, indicating that they will be mechanically robust for removal up to this period.

In some embodiments, the implant includes a pure polymer coating and/or a pure polymer core that can be used to further modulate and tune drug release.

BRIEF DESCRIPTION OF THE DRAWINGS

FIGS. 1A, 1B, and 1C show side, bottom, and top views (respectively) of an exemplary device for making a concentrated polymer drug solution (100). FIGS. 1D and 1E show side views of alternative versions of an exemplary top plunger (110a, 110b). FIG. 1F shows a side view of an exemplary bottom plunger (120).

FIGS. 3A-3E are graphs depicting levonorgestrel (LNG) release from various implants, measured in vitro. FIGS. 3A and 3B show LNG release from implants generated by Methods 1 and 2, respectively. FIGS. 3C and 3D show LNG release from disc and rod implants (respectively) generated by Method 3. FIG. 3E shows LNG release from a commercial implant that was used as a positive control.

DETAILED DESCRIPTION OF THE INVENTION

I. Definitions

Figure 2B:
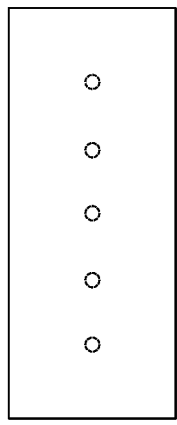
FIGS. 2A, 2B, and 2C show side, top, and bottom views (respectively) of an exemplary heavy plunger (200a), configured to insert into a baking mold (200b).
Figure 2C:
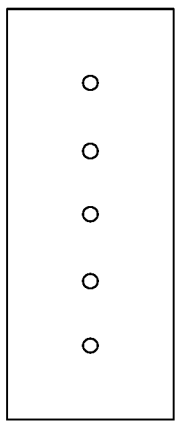
Figure 2F:
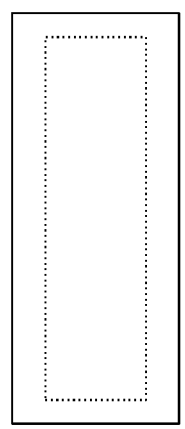
FIGS. 2D, 2E, and 2F show side, top, and bottom views (respectively) of an exemplary baking mold (200b).

The term "biocompatible" as used herein, generally refers to materials that are, along with any metabolites or degradation products thereof, generally non-toxic to the recipient, and do not cause any significant adverse effects to the recipient. Generally speaking biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to years.

The term "contraceptive" as used herein, generally refers to a method or device serving to prevent pregnancy.

The term "copolymer" as used herein, generally refers to a single polymeric material that is comprised of two or more different monomers. The copolymer can be of any form, such as random, block, graft, etc. The copolymers can have any end-group, including capped or acid end groups.

The term "diagnostic agent", as used herein, generally refers to an agent that can be administered to reveal, pinpoint, and define the localization of a pathological process.

The term "implant", as used herein, generally refers to a device that is inserted into the body.

The term "nanoparticle", as used herein, generally refers to a particle having a diameter, such as an average diameter, from about 10 nm up to but not including about 1 micron, preferably from 100 nm to about 1 micron. The particle can have any shape. Nanoparticles having a spherical shape are generally referred to as "nanospheres".

The term "prophylactic agent", as used herein, generally refers to an agent that can be administered to prevent disease or to prevent certain conditions like pregnancy.

The term "subcutaneous implantation", as used herein, generally refers to an implantation under the skin.

The term "therapeutic agent", as used herein, generally refers to an agent that can be administered to prevent or treat one or more symptoms of a disease or disorder. Examples include, but are not limited to, a nucleic acid, a nucleic acid analog, a small molecule, a peptidomimetic, a protein, peptide, carbohydrate or sugar, lipid, or surfactant, or a combination thereof.

II. Compositions

The compositions described herein include implants formed of degradable polymers, having therapeutic, prophylactic and/or diagnostic agents incorporated therein or thereon, and, optionally, pharmaceutically acceptable additives. In a preferred embodiment, the implant degrades over a period of time, for example 18 months, 24 months, 30 month, 36 months, etc., thus eliminating the need for removal by a trained practitioner.

The period during which the device is removable might be the same or different then the period of release. In this context, removable or removability means the implant retain sufficient mechanical properties to be removed (e.g., before or after release is complete), typically using forceps to physically withdraw the implant from under the skin. As introduced above, some implants are never removed because they fully degrade.

In some embodiments, degradation is complete within 6 months of the end of release. For example, in some embodiments, product can be removable for a period equal to the period of efficacy minus about six months. In preferred embodiments, the implant degrades within about six month after the period of efficacy. For example, in some embodiments, drug (e.g., LNG) release occurs over a period of preferably 12-18 months, but implant degradation occurs over a period of 18 to 36 months. In other embodiments, the implant can be removable for up to a year or up to 18 months, with 18 months or 24 months of efficacy. In a particular embodiment, the implant is removable for up to a year with 18 months of efficacy.

A. Copolymers i. Poly(ω-pentadecalatone-co-p-dioxanone) [poly(PDL-co-DO)]

Poly(PDL-co-DO) is a family of degradable polyester copolymers that degrade slowly in the presence of water. Poly(PDL-co-DO) copolymers are formed by ring-opening copolymerization of o-pentadecalatone (PDL) and p-dioxanone (DO) and have the general Formula (I):

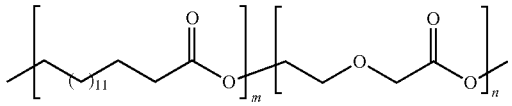

Formula (I)

wherein n and m are independently integer values of less than or equal to about 1500.

Poly(PDL-co-DO) copolymers have tunable biodegradability and physical properties based on the molar feed ratio of the o-pentadecalatone and p-dioxanone comonomers used in the copolymer synthesis. In certain embodiments, the molar ratio of PDL to DO is approximately about 99:1, 95:5; 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, and 1:99. In some embodiments, the molar feed ratio is in a range of about 99:1 to 1:99, or between any two values given above. In some embodiments, the poly(PDL-co-DO) copolymers have a DO mol % content of about 1, 5, 10, 15, 20, 25, 30, 35, 40, 45, 50, 55, 60, 65, 70, 75, 80, 85, 90, 95, or 99%. In some embodiments, the DO mol % content of the copolymers is in a range of about 1 to 99%, or between any two values given above. The DO mol % content can be determined from the $^1$H NMR of the copolymer. In embodiments, the DO mol % is between about 25% and 65% inclusive. Preferred values for this application seem to be 30-50% DO. In specific embodiments, the DO mol % content 27%, 28%, 38%, or 60%.

The copolymers described can have any molecular weight. The copolymer generally has a weight average molecular weight of at least 10,000 g/mol, at least 20,000 g/mol, at least 25,000 g/mol, at least 40,000 g/mol, at least 50,000 g/mol, at least 60,000 g/mol, at least 75,000 g/mol, at least 90,000 g/mol, at least 100,000 g/mol, at least 120,000 g/mol, at least 150,000 g/mol, at least 200,000 g/mol, at least 250,000 g/mol, at least 400,000 g/mol, at least 500,000 g/mol, or at least 750,000 g/mol. In preferred embodiments the weight average molecular weight of the Poly(PDL-co-DO) copolymers is in the range of about 25,000 g/mol to about 100,000 g/mol, more preferably about 50,000 to about 75,000 g/mol based on, for example, gel permeation chromatography (GPC) relative to polystyrene standards. The copolymers can have a polydispersity index (PDI) in the range of about 1 to about 6, more preferably about 2 to about 4, and even more preferably about 1.5 to about 2.5.

In exemplary embodiments, the copolymers have a DO content (Mol %) and Mw accordingly to the chart below.

TABLE 1

DO content (Mol %) and Mw

| DO content (Mol %) | Mw | Mw/Mn |
|---|---|---|
| 27% | 114800 | 2.2 |
| 27% | 122200 | 2.2 |
| 38% | 108000 | 2.1 |
| 38% | 108300 | 2.2 |
| 59% | 76600 | 1.8 |
| 60% | 70100 | 1.8 |

The copolymers can possess any degree of crystallinity. In certain embodiments, the degree of crystallinity of the copolymers is about 10, 20, 30, 40, 50, 60, 70, 80 or 90% as determined by methods such as wide-angle X-ray scattering (WAXS). The copolymers have thermal degradation temperatures of up to 425° C., which can be determined by thermal gravimetric analysis (TGA) of the copolymer. In certain embodiments, the thermal degradation temperatures of the copolymers can be up to about 300° C., 325° C., 350° C., 375° C., 400° C., or 425° C.

B. Polymer Additives

Pharmaceutically acceptable additives may be incorporated with the poly(PDL-co-DO) copolymers and compositions prepared with the copolymers prior to converting these compositions into implants. These additives can be incorporated during the formation of an agent loaded polymer composition which can be subsequently processed into implants. For example, additives may be combined with the poly(PDL-co-DO) copolymers and agent(s) and the resulting pellets or films can be compressed or extruded into implants. In another embodiment, the additives may be incorporated using a solution-based process. In a preferred embodiment, the additives are biocompatible, biodegradable, and/or bioabsorbable.

In certain embodiments, the additives may include, but are not limited to plasticizers. These additives may be added in sufficient quantity to produce the desired result. In general, these additives may be added in amounts of up to 20% by weight. Plasticizers that may be incorporated into the compositions include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof.

C. Contraceptive Agents

In a preferred embodiment, the agent is of prophylactic nature, preferably a contraceptive agent. The contraceptive agent can be for female contraception or male contraception. In some embodiments, two or more contraceptive agent are used. The contraceptive agent can be steroidal or non-steroidal.

In some embodiments, the contraceptive agent includes a estrogen formulation, a progestin formulation, or combined estrogen and progestin formulations. Contraceptive agent(s) may be progestogen agents or from progesterone receptor modulators. Progestogen agents, also designated progestins, may be any progestationally active compound. The progestogen agents may be progesterone and its derivatives such as, but not limited to, 17-hydroxy progesterone esters, 19-nor-17-hydroxy progesterone esters, 17-alpha-ethinyltestosterone and derivatives thereof, 17-alpha-ethinyl-19-nortestosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgesterol, DL-norgestrel. D-17-alpha-acetoxy-13-beta-ethyl-17-alpha-ethinyl-gon-4-en-3-one oxime, gestodene, desogestrel, DMPA-depo medroxyprogesterone acetate, norgestimate, nestorone and drospirenone. Progesterone receptor modulators may be ulipristal acetate, mifepristone or CDB-4124 or active metabolites thereof.

Preferably, the contraceptive agent is levonorgestrel (LNG), a synthetic progestin having the following chemical structure:

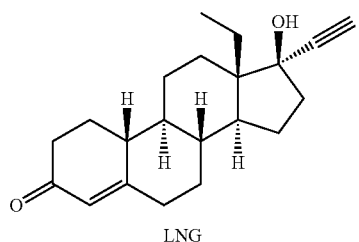

LNG

LNG prevents pregnancy by preventing the release of an egg from the ovary or by preventing fertilization of the egg by sperm. LNG may also function by changing the lining of the uterus, thus preventing implantation of a fertilized egg.

The percent drug loading is typically from about 1% to about 80%, from about 1% to about 50%, from about 1% to about 40% by weight, from about 1% to about 20% by weight, or from about 1% to about 10% by weight. In some embodiments, the percent drug loading is between about 5% and about 50%, or about 10% and about 40%, or about 15% and about 30%. In specific embodiments, drug loading is about 20, 21, 23, 24, 25, 26, 27, 28, 20, or 30%.

In preferred embodiments, the weight ratio of copolymer to one or more agents is about 3:1, 2.5:1, 2:1, 1:1, or between any two of the aforementioned ratios.

D. Other Therapeutic, Prophylactic and Diagnostic Agents

Active agents include synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and oligonucleotides), sugars and polysaccharides, small molecules (typically under 1000 Daltons), lipids and lipoproteins, and biologically active portions thereof. Suitable active agents have a size greater than about 1,000 Da for small peptides and polypeptides, more typically at least about 5,000 Da and often 10,000 Da or more for proteins. Nucleic acids are more typically listed in terms of base pairs or bases (collectively "bp").

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), danazole, and combinations thereof. Other suitable anti-cancer agents include angiogenesis inhibitors; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; and transforming growth factor-α or transforming growth factor-β inhibitors.

Other therapeutics that may be delivered with this technology include antibiotics (antibacterial, antiviral or antifungal), antiinflammatory (such as steroids like cortisone and prednisone and non-steroidal antiinflammatories such as naproxan), and local anesthetics such as lidocaine, for release at the time of and shortly after implantation to minimize any swelling or infection.

Imaging agents such as radioopaque compounds may also be incorporated to facilitate localization at the time of placement or removal.

III. Methods of Making

A. Methods of Making Copolymers

Poly(PDL-co-DO) can be synthesized by ring-opening copolymerization of o-pentadecalactone (PDL) with p-dioxanone (DO) as illustrated below and disclosed in Jiang et al. (*Biomacromolecules* 8:2262-2269; 2007):

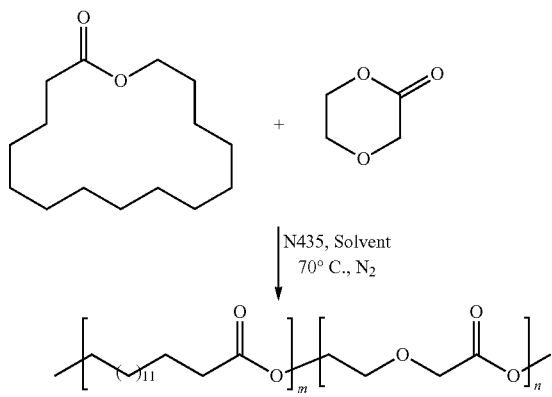

In preferred embodiments, the poly(PDL-co-DO) copolymers are enzymatically synthesized using metal-free reaction conditions.

In a non-limiting example, NOVOZYM 435 (5 wt % vs total monomer) catalyzed copolymerizations of PDL and DO co-monomers and were conducted in anhydrous toluene or diphenyl ether (200 wt % vs total monomer) at 70° C. under nitrogen for 26 hours. To synthesize copolymers with different PDL or DO contents, various PDUIDO monomer feed ratios can be used, as described above.

B. Methods of Making Devices

1. Methods of Making Implants

The biodegradable implants formed of a copolyester encapsulating one or more contraceptive agents can be formed by molding, compression, extrusion, or other polymer processing methods. In some embodiments, the implant is formed using a mold. The mold can be made from any suitable material.

The implants can have a rod, bar, disc, or plate shape of any dimension which is suitable for implantation into the body. The implants formed by the methods described do not include or form nanoparticles, nor are they injectable using a needle (gauge 14 or smaller) and syringe.

In some embodiments, the implants are cylindrical rods of various lengths. In certain embodiments the length of the cylindrical rod shaped implants is in the range of about 0.1 to about 20 mm and the diameter of the implants is in the range of about 0.1 to about 5 mm. In preferred embodiments, the cylindrical rod shaped implants are about 13 mm in length and 2.4 mm in diameter.

In one non-limiting method of making the biodegradable implant, the method includes the steps of:

(1) preparing a solution of a biocompatible polyester copolymer and a contraceptive agent in a suitable solvent to form a composition including the copolymer and the agent;

(2) loading the composition into a mold; and (3) forming the implant.

In some embodiments step (1) includes drawing the solution of the composition into a pipette and removing the solvent, such as by evaporation at atmospheric pressure or under vacuum, to form one or more pellets comprising the copolymer and the agent.

In certain embodiments the mold of step (2) is an evaporation or baking mold. Non-limiting examples of molds which can be used according to the methods described are shown in FIGS. 1A-1F and 2A-2F. Step (2) can further include spinning or centrifuging the evaporation mold, at a suitable centrifugal force, while under vacuum to remove the solvent in order to form one or more pellets comprising the copolymer and the agent. In certain embodiments, step (2) can further include a baking step performed under an inert atmosphere. Baking is typically carried out at a temperature in the range of about 50° C. to about 100° C. for a period of time in the range of about 0.1 to about 24 hours, more preferably 1 to 10 hours.

In step (3) of the general method described above, forming the implant may include the application of pressure to compress the composition, which is formed of the one or more pellets formed in either step (1) or (2), in the mold and which can be followed by a baking step typically performed under an inert atmosphere. Baking is typically carried out at a temperature in the range of about 50° C. to about 100° C. for a period of time in the range of about 0.1 to about 24 hours, more preferably 1 to 10 hours.

In certain embodiments, step (1) includes forming the composition into a film. In a non-limiting example, a film may be formed by adding the solution of step (1) into water and removing the solvent (such as by rotary evaporation) to afford a film. The resulting film can be optionally subjected to lyophilization to remove excess water.

In certain embodiments, the implant formed in step (3) is formed by extrusion of the composition. Extrusion is a particularly preferred method of manufacture, and empirical evidence shows that the materials form suitable implants when formed in this way.

In preferred embodiments of the method, the biocompatible polyester copolymer forming the implant is poly(w-pentadecalactone-co-p-dioxanone), as described above, and the prophylactic agent is the contraceptive drug levonorgestrel (LNG).

Other non-limiting methods of making the biodegradable implants encapsulating drug include, for example:

a. Micropipette Loading of Drug/Polymer

In this method the polymer and the agent are dissolved in dichloromethane (DCM). The solution is drawn into a glass micropipette, and the DCM is evaporated to form polymer/drug pellets. The pellets can be injected into a mold, preferably a TEFLON® mold, compressed with a steel rod, and baked under argon protection. Preferably, the implant is then cooled overnight after baking.

b. Centrifugal Loading of Drug/Polymer

The polymer and agent are dissolved in DCM. The polymer/drug solution is then loaded into a custom-built evaporation insert and centrifuged under vacuum to produce a pellet. The pellet is injected into a mold, such as a Teflon mold, for example. The material is baked under argon protection and compressed with a steel rod. Preferably, the implant is then cooled overnight after baking.

c. Film Production and Manual Loading of Drug/Polymer

The polymer and agent are co-dissolved in DCM. The polymer/drug solution is then added to water in a rotary evaporator. The polymer/drug film precipitates out of solution as the DCM evaporates. The material can then be recovered, lyophilized and loaded into a mold. The material is baked in the mold under argon protection for two hours and then immediately compressed with a modified heavy plunger.

The foregoing is exemplary. It is understood that other methods can be used, and that modifications will be required to scale up production.

2. Coated Implants, Core implants, and Coated+Core Implants

Figure 11:
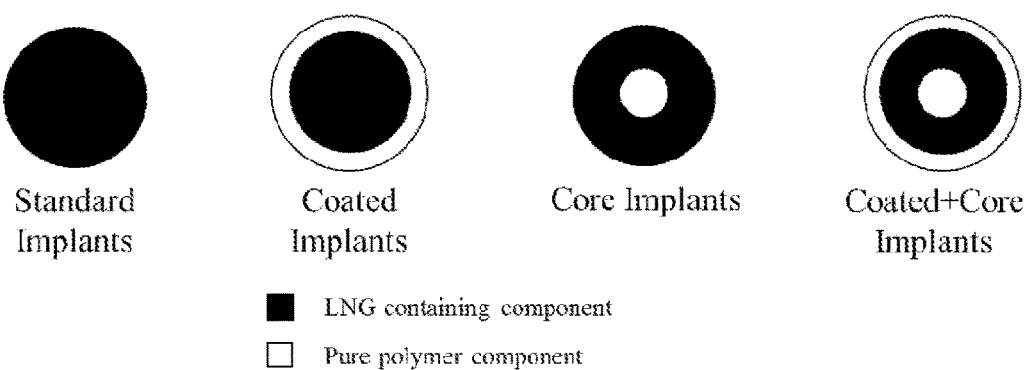
FIG. 11 is an illustration comparing various exemplary implant embodiments including standard implants, coated implants having a drug-free sheet or film coating around a standard drug-containing implant, core implants having a drug-free core within a standard drug-containing implant, coated+core implants having a drug-free core and coating.

The disclosed implants can include a coating or film, a core, or a combination thereof. The coating and the core can be drug-containing or drug-free. For example, implants can contain a drug-free (also referred to herein as "pure polymer") core to shorten the final drug release tail. Additionally or alternatively, the implants can include a drug-free (i.e., pure polymer) coating to reduce initial burst release. Exemplary, non-limiting embodiments are illustrated in FIG. 11.

In an exemplary method for pure polymer core fabrication, polymer is loaded inside a baking mold (e.g., (d=1 mm)) and baked to create pure polymer core.

Coated implants can be fabricated by preparing a polymer sheet and coating the polymer sheet on the implant.

In an exemplary method for polymer sheet fabrication, a polymer sheet is formed by dissolving PDL-co-DO in chloroform, pouring the solution into glass Petri dish, allowing chloroform to evaporate (e.g., over night at room temperature), and harvesting the PDL-co-DO sheet.

In an exemplary method for coating polymer sheets onto implants, an implant is sandwiched between two polymer sheets and placed inside a baking mold and allowed to bake (e.g., for 10 min at 70-80° C. in atmosphere pressure with argon protection).

In some embodiments, the coating sheet includes drug. In an exemplary embodiment PDL-co-DO (DO context of, for example, 36%) polymer and LNG (LNG loading is kept constant at, for example, 20%).

In preferred embodiments, the coating is drug-free and is effective to reduce any initial burst effect of drug released from the implant relative to an uncoated implant.

After coating, excess polymer can be cut from the implant.

In an exemplary method for preparing pure polymer film, pure polymer is loaded onto aluminum foil at the base of a mold and compressed using a plunger. The polymer-containing mold is baked (e.g., at 90-100° C. for about 1 hr), removed from the heat, compressed, and allowed to cool (e.g., overnight.).

Similarly, drug-loaded film can be prepared by mixing polymer and drug, loading the mixture inside the mold on a sheet of aluminum foil, compressing the mixture using the plunger and baking it (e.g., for about 1 h at 90-100° C.). The film can be compressed again and cooled down.

The mold and plunger/compressor can be used in this fashion to tune the film to various desired thicknesses.

As discussed above and in exemplified in the working Examples below, the films can be formed by solvent evaporation from solutions of polymer/solvent which can be referred to by weight/volume as a percentage. For example, in some embodiments, the coating is between about 5% and 50%, or between about 10% and 30%, or between about 15% and 25%, or about 15, 16, 17, 18, 19, 20, 21, 22, 23, 24, or 25% PDL-co-DO. Higher and lower percentages are also envisioned. In particular embodiments, the percentage is between about 5% and about 60% inclusive, or any discrete integer between about 5% and about 60% inclusive.

Generally, the desired thickness of the coating and/or core can be one that is effective to reduce release rates, and/or reduce or eliminate a burst or tail of non-linear drug release from the implant. The burst or tail can be at the beginning, end, or an intermediate stage of drug release. In some embodiments, the coated and/or cored implants maintain zero order release kinetics despite having a drug-free coating and/or core.

The some embodiments, the thickness of a coating is at least about several hundred microns. For example, in some embodiments, the thickness is from around 0.3 mm to 1 mm, or about 0.4 mm to about 0.6 mm. These thickness ranges are appropriate for 1, 2, 3, and 4 cm implants.

In some embodiments, a pure polymer sheet is fabricated by a casting method (e.g., casting the thick pure polymer solution on to glass petri dish, allow organic solvent to dry and harvest the sheet).

In some embodiments, the DO mol % content in two or more of the coating, the core, and the implant are the same or different. For example, in some embodiments, the DO mol % of the coating is lower or higher than DO mol % of the implant. The DO mol % content discussed in greater detail about with respect to the implant, can thus also be utilized in the coating and/or the core. In a particular exemplary embodiment, the DO mol % of the coating and/or the core is between about 25% and about 75%. A particularly embodiment, the DO mol % of the coating is about 37%, which may be a preferred DO mol % to prevent initial burst.

In some embodiments, the film or coating is prepared with a three-part molding system: from top to bottom are the plunger that can be used to compress the polymer into shape, the middle molding chamber that is a lumen, and the bottom platform (base). The middle molding chamber can be separate from the base platform to allow easy access and harvest of the fabricated polymer sheet, and to allow insertion of different materials (i.e. aluminum sheet, paper) as a layer for polymer sheet to form on.

An exemplary sheet compressor mold including a mold base (300), a shaping mold (310), and a compressor (320), are depicted in FIGS. 13A-15C. The compressor (320) (FIGS. 15A-15C) has a flange portion (324) and a plunger portion (325). The shaping mold (310) (FIGS. 14A-14C) includes a base portion (311) as well as a cylindrical molding chamber (314) having a cavity (315) capable of receiving the plunger portion (325) of the compressor (320). The mold base (300) (FIGS. 13A-13C) can be secured to the base portion (311) of the shaping mold (310) (FIGS. 14A-14C) using screws that traverse the screw holes (302) in the mold base (300) and corresponding screw holes (312) in the shaping mold (310). The figures exemplify a mold base (300) and shaping mold (310) each with four screw holes (302, 312).

In a particular embodiment, the screw holes (302, 312) have a diameter of 0.9 cm; the mold base (300) and the base portion (311) of the shaping mold (310) are 8 cm×8 cm; the width of the cylindrical wall (316) of the molding chamber (314) is 1 cm; and the diameter (318) of the cavity (315) is 4 cm.

Mold use is important to fabrication. Molds can be used to fabricate implants on a small scale, and can be used to fabricate implants on a larger scale, using multiple molds at once. The implant may be fabricated through, for example, twin screw, or hot-melt extrusion.

All of the foregoing is exemplary. It is understood that other methods can be used, and that modifications will be required to scale up production.

IV. Methods of Use

In preferred embodiments, implants are effective in preventing pregnancy.

Implants are to be placed under standard surgical procedures, which may include laparoscopically or injection through a catheter or small incision in the skin in the same manner as the other contraceptive implants that are nondegradable, such as NORPLANT® and JADELLE®. In preferred embodiments, implants are implanted subcutaneously or subdermally, for example, using a trocar. A local anesthetic is applied and an incision is made down to the subcutaneous layer of the skin. This creates a pocket in which the implant will be inserted. The incision is stitched shut after placement of the implant. Application of surgical tape can minimize movement of the implant while the skin fuses around the implant.

In some embodiments, the implant is administered via a large gauge needle or a trocar.

The precise dosage administered to a patient will depend on many factors, including the length of time over which drug is to be released and the specific drug being released.

The preferred doses for clinical application are the same as JADELLE® or NORPLANT®. JADELLE® consists of two rods, each with 75 mg of LNG, and works for five years. NORPLANT® consists of six SILASTIC® capsules, each containing 36 mg of the progestin, LNG and works for five years. In the preferred embodiment of the biodegradable implant, the device consists of one rod, retaining mechanical integrity for 18 months, therefore containing and releasing approximately 45 mg LNG over the period. In one preferred embodiment, the implant contains 50 mg of poly(pentadecalactone-co-dioxanone) and 20 mg of LNG. In some embodiments, an implant does not release all of the loaded drug.

The present invention will be further understood by reference to the following non-limiting examples.

EXAMPLES

Example 1. Synthesis of Poly(pentadecalactone-co-dioxanone (PDL-co-DO)) Copolymers Materials and Methods A reaction mixture containing ω-pentadecalactone (PDL), p-dioxanone (DO), and Novozym 435 (5 wt % vs total monomer, dried under 1.0 mmHg at 40° C. for 20 h) in toluene (200 wt % vs total monomer) was magnetically stirred at 70° C. under nitrogen (1 atm) for 26 hours. At the end of the reaction, the product mixture was dissolved in chloroform, and the resultant solution was filtered to remove the catalyst particles. The filtrate was then concentrated at 30-40° C. under vacuum. A white solid precipitate was obtained by adding the concentrated polymer solution into magnetically stirred methanol drop by drop. The precipitated polymer was filtered, washed with methanol three times, and then dried overnight at 40° C. under vacuum.

The number-average molecular weights and weight-average molecular weights ($M_n$ and $M_w$, respectively) of poly (PDL-co-DO) copolyesters were measured by gel permeation chromatography (GPC) using chloroform as the eluent and narrow polydispersity polystyrenes as the standards. The molecular structure and composition of the copolymers were analyzed by proton and carbon-13 NMR spectroscopy (as described in Jiang et al. *Biomacromolecules*, 8:2262-2269; 2007).

Results

Polymers were successfully synthesized and characterized. The polymer have the properties described in the table below.

TABLE 2

Typical Batches of Poly(PDL-co-DO) Samples

| Sample ID | PDL/DO (feed molar ratio) | DO Content (mol %) | $M_w$ | $M_w/M_n$ |
|---|---|---|---|---|
| P062513-1 | 30:70 | 60% | 52000 | 2.1 |
| P062513-2 | 40:60 | 50% | 60500 | 1.9 |
| P062513-3 | 50:50 | 39% | 62200 | 2.0 |
| P062513-4 | 60:40 | 30% | 61300 | 2.1 |
| P062513-5 | 70:30 | 22% | 68500 | 2.1 |

Example 2. Fabrication of Implant

Methods

A number of methods for the production of contraceptive implants were developed. In all cases, the active pharmaceutical ingredient (API) was levonorgestrel (LNG). All of the methods used a custom-made TEFLON® mold, which could be loaded with up to 5 implants (FIGS. 2A-2F). In most cases (unless specified), the implant was a cylindrical rod of approximately 13 mm in length and 2.4 mm in diameter.

Unless otherwise specified, the implant was baked under argon at atmospheric pressure at 70° C. for 9 hours. Unless otherwise specified, the implant was cooled overnight after baking. Typical implants were produced with 50 mg of polymer and 20 mg of drug.

Method 1—Fabrication of Implant by Micropipette Loading of Levonorgestrel (LNG)/poly-(PDL-co-DO) 50 mg of polymer and 25 mg of LNG were dissolved in 400 μl of dichloromethane (DCM). The solution was drawn into a glass micropipette (Drummond Scientific Company, WIRETROL® II). DCM was evaporated at room temperature and atmospheric pressure for 24 hours to form white pellets of polymer/drug. The pellets were injected into a TEFLON® mold (FIG. 2D; 200b), compressed with a stainless steel rod (FIG. 2A; 200a) and baked under argon protection at atmospheric pressure for 10 hours at 60° C.

Method 2—Fabrication of Implant by Centrifugal Loading of LNG/poly-(PDL-co-DO)

50 mg of polymer and 20 mg of LNG were dissolved in 1 ml of DCM. The polymer/drug solution was loaded into a custom built evaporation mold (FIG. 1A; 100) and spun at 1300 RPM under vacuum for approximately 30 minutes to remove all of the DCM. The polymer/drug pellet was injected into a baking mold (FIG. 2D; 200b), and baked under argon protection at atmospheric pressure for 10 hours at 60° C. The implants were manually compressed immediately after baking using a stainless steel rod (FIG. 2A; 200A) to reduce porosity.

Method 3—Fabrication of Implant by Film Production and Manual Loading of LNG/poly-(PDL-co-DO)

Figure 2A:
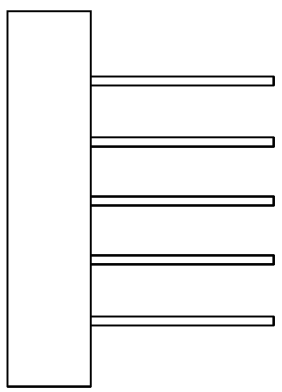
Figure 2D:
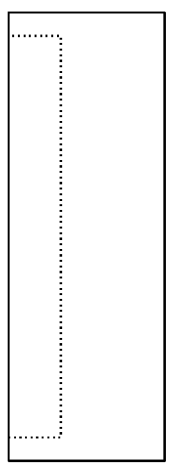
Figure 2E:
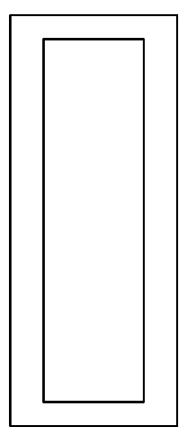

200 mg of polymer and 60 mg of LNG were dissolved in 15 ml of DCM. The polymer/drug solution was added to a round bottom flask containing 50 ml of deionized water and placed on a rotary evaporator for 20 minutes to remove the DCM. The resultant polymer/drug film was lyophilized to remove excess water. 120 mg of the polymer/drug film was then loaded into a baking mold (FIG. 2D; 200b), and baked under argon protection at atmospheric pressure for 2 hours at 90° C. The implant was compressed immediately after baking using a stainless steel plunger and allowed to cool overnight (FIG. 2A; 200a)

The implant shown in FIG. 3C is made by forming the polymer/drug solution into a thin sheet and cutting it into discs, as a preliminary model of an implant. The rod shown in FIG. 3D was made in the same relative dimensions and shape as non-degradable implants so that they could be implanted with the same procedure and using the same trochars that health care providers are already familiar with.

Method 4—Extrusion of Polymer

A HAAKE MiniCTW Micro-Conical Twin Screw Compounder was used for extrusion. Pure polymer was extruded at 55° C. and at 50 RPM. The resultant implant was smooth and uniform. Pure polymer extruded at 65° C. and at 50 RPM resulted in fragile, non-uniform rods.

SEM Analysis of Implant Sections

After freezing to the optimal cutting temperature, portions of completed implants were sectioned at a thickness of 30 μm using a cryomicrotome. Sections were then mounted on stubs, sputter coated, and imaged using scanning electron microscopy (SEM). Prior to implantation, implants were sterilized by UV radiation for 10 minutes.

Figure 4:
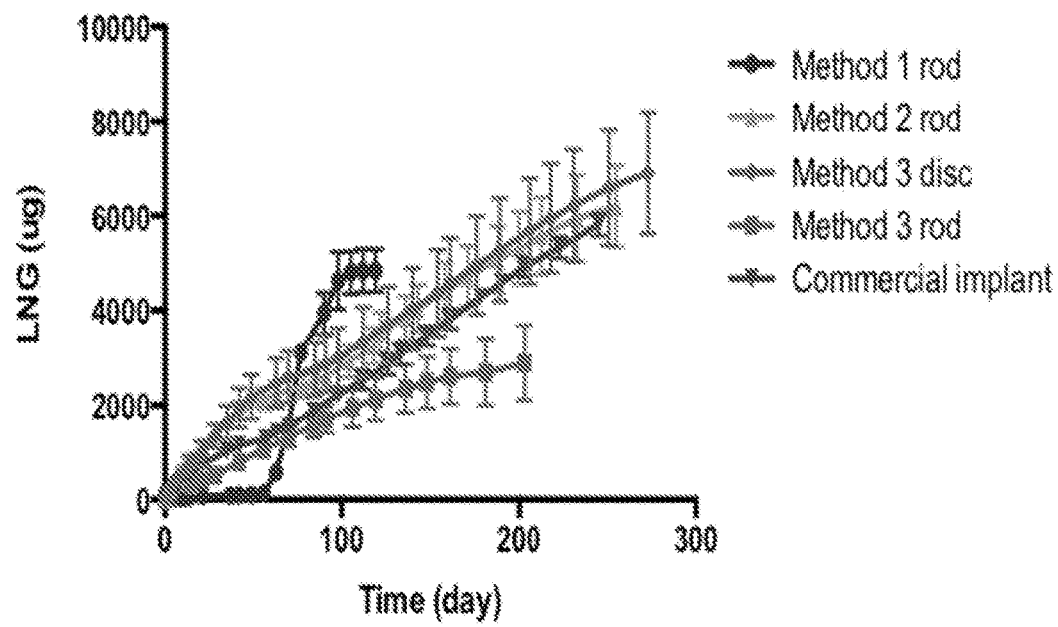
FIG. 4 is a graph depicting a comparison of levonorgestrel (LNG) release in vitro from implants produced by different fabrication methods.

Results Implants produced by Methods 1, 2, and 3 as described above were studied for their ability to release LNG during continuous incubation in buffered saline solutions at 37° C. (FIGS. 3A-3E and FIG. 4). Optimal implants provided LNG release that was similar to the pattern of release observed from a commercial implant, known as SUSUK KB II, which is produced by Shanghai Dahua Pharmaceutical Co. Ltd. PRC and is used in Indonesia (English name being SINO-IMPLANT II®) (FIG. 4). The SUSUK KB II implant is composed of LNG encapsulated in a silicon capsule. Each SUSUK KB II implant contains 75 mg LNG and is effective for 3 years.

Initial drug loading level is a key factor in determining the kinetics of release (FIG. 5). The implants were found to be mechanically stable after nearly 300 days of continuous incubation in buffered saline at 37° C.

Example 3. Analysis of Drug Release from Implants

In Vitro Methods

Drug Release and Polymer Degradation Assay

Initially implants were incubated in 1 ml of 25% ethanol 1× phosphate buffered saline (PBS) solution at 37° C. At around 100 days, polymer implants had degraded significantly due to the presence of ethanol in the incubating buffer. Release studies were then restarted by incubating implants in 1 ml of 3% Methyl-beta-Cyclodextrin (M-β-CD), 1×PBS (pH=7.4) buffer solution at 37° C. For the drug release study, samples were drawn from the buffer every week during the first 2 months and every two weeks after that. Samples were analyzed for drug content using HPLC. For the polymer degradation assay, implant samples were collected every month and washed with diH$_2$O, dried and analyzed by GPC.

HPLC Conditions

A Waters C18 column (WAT086684) was used for levonorgestrel (LNG) quantification. A gradient method was applied to resolve the LNG each time. Solvent A was prepared by adding TFA to HPLC grade water (0.1% v/v). Solvent B was prepared by adding TFA to HPLC grade acetonitrile (0.1% v/v). LNG was detected at 240 nm.

Measurement of Polymer Molecular Weight by Gel Permeation Chromatography

The number and weight average molecular weights ($M_n$ and $M_w$, respectively) of polymers were measured by gel permeation chromatography (GPC) using a Waters HPLC system equipped with a model 1515 isocratic pump, a 717 plus autosampler, and a 2414 refractive index (RI) detector with Waters Styragel columns HT6E and HT2 in series. Empower II GPC software was used for running the GPC instrument and for calculations. Both the Styragel columns and the RI detector were heated and maintained at 40° C. temperature during sample analysis. Chloroform was used as the eluent at a flow rate of 1.0 mL/min. Sample concentrations of 2 mg/mL and injection volumes of 100 μL were used. Polymer molecular weights were determined based on a conventional calibration curve generated by narrow polydispersity polystyrene standards from Aldrich Chemical Co.

In Vitro Results

Figure 6:
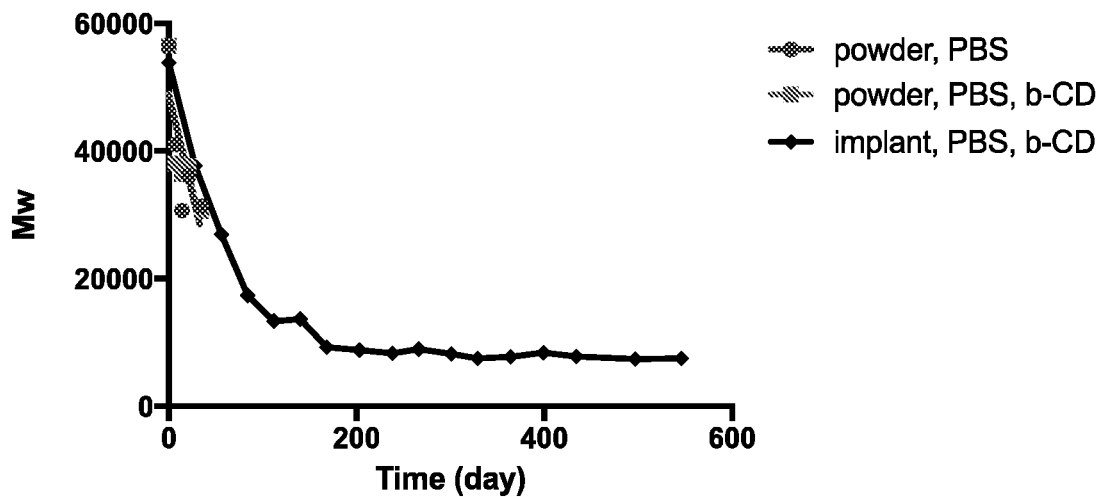
FIG. 6 is a graph depicting degradation of poly(PDL-co-DO) during continuous incubation in buffered saline at 37° C.

The internal structure of the implant materials suggests that there is phase separation, with some evidence of crystals of LNG dispersed throughout the polymer matrix. As shown in FIG. 6, resultant polymer degradation occurred in a gradual fashion over the course of approximately 25 weeks. The molecular weight of the poly(PDL-co-DO) decreases with incubation time (FIG. 6), but slows after an initial decrease during the first 10 weeks. The initial decrease in molecular weight is likely due to hydrolysis of DO-rich regions of the polymer, since these regions likely allow easier water entry and are more susceptible to hydrolysis.

In Vivo Methods

Thirty female C57/BL6 mice of around 20 g in weight were used for the biocompatibility study. Fifteen mice received the commercial implant while the other 15 received the poly-(PDL-co-DO)/LNG implants. Implants were fabricated according to Method 3, were cut into 5 mm lengths, and sterilized by UV radiation for 10 minutes. Animals were placed under isoflurane using a precision vaporizer, and were maintained under isoflurane during the entire surgical procedure. After anesthesia, the backs of the mice were shaved and sterilized with betadine and alcohol wipes. Subcutaneous pockets were created by clearing connective tissue under the skin by careful blunt dissection. Implants were inserted into the subcutaneous pocket and the incision site closed using an auto clipper. Mice received 0.3 mg/kg meloxicam every day for 3 days after implantation for pain management. At 2, 4, and 6 months post-implantation, five random mice from each group were sacrificed. Animals were shaved and implant site was located. An incision was created from the abdomen of the animal and cut towards the direction of the implant site. Tissue around the implant site was harvested and analyzed for encapsulation and inflammation.

Combined Results of In Vitro and In Vivo Methods

Results of in vitro and in vivo studies were compared to results obtained with the commercial implant, SUSUK KB II (English name being SINO-IMPLANT (II)®). SINO-IMPLANT (II)® is composed of two thin, flexible 4 cm long silicone rods, where each rod contains 75 mg of LNG (150 mg total). It is registered in China by the SFDA for three years of continuous use. SINO-IMPLANT (II)® is one of the most effective contraceptive methods available globally, with annual pregnancy rates of less than 1 percent. After removal of this implant, there is no delay in a woman's return to fertility compared to women who are not using a contraceptive method. Worldwide, over 8 million women have used SINO-IMPLANT (II)® since 1994. The product is registered under various names in different countries including ZARIN®, FEMPLANT, SIMPLANT®, and TRUST.

Optimal implants provided LNG release that was similar to the pattern of release observed from the commercial implant (FIG. 4).

Implants were also examined after 2 years and 2.5 years of in vitro drug release. Two made using Method 2 were harvested at day 932. Two made using Method 3 were harvested at day 714. LNG was (or will be) measured using HPLC.

TABLE 3

Total Weight and LNG Weight After Implant Removal

| Implant | LNG left (mg) | Total weight (mg) |
|---|---|---|
| Method 2 | Not detected | 7 |
| Method 2 | 1.04 | 19 |
| Method 3 | 0.53 | 14 |
| Method 3 | 0.61 | 14 |

Figure 5A:
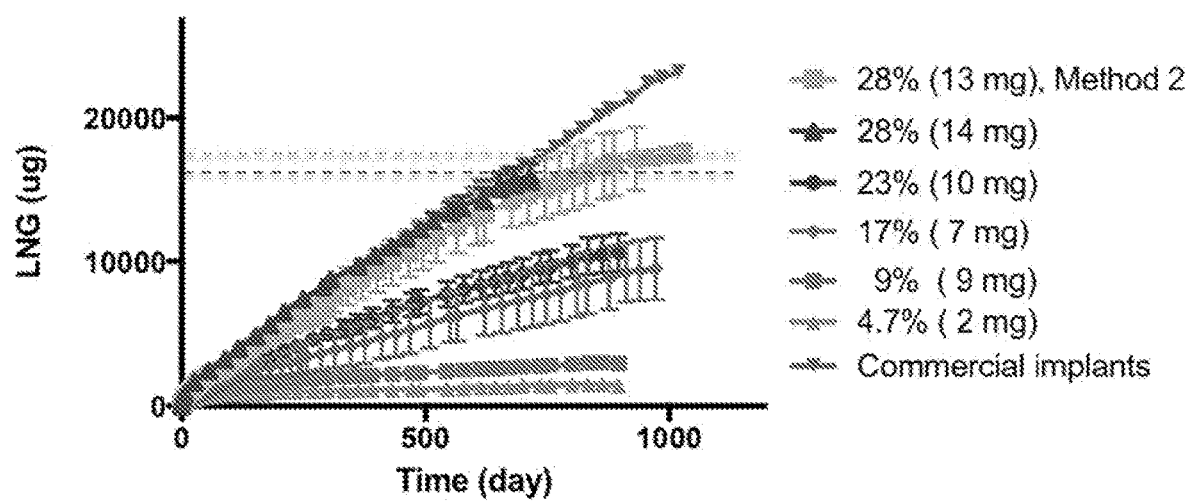
FIG. 5A is a graph that depicts the effect of LNG initial loading on LNG release from implants in vitro.

Initial drug loading level is a key factor in determining the kinetics of release (FIG. 5A). The implants were found to be mechanically stable after nearly 300 days of continuous incubation in buffered saline at 37° C.

Figure 5B:
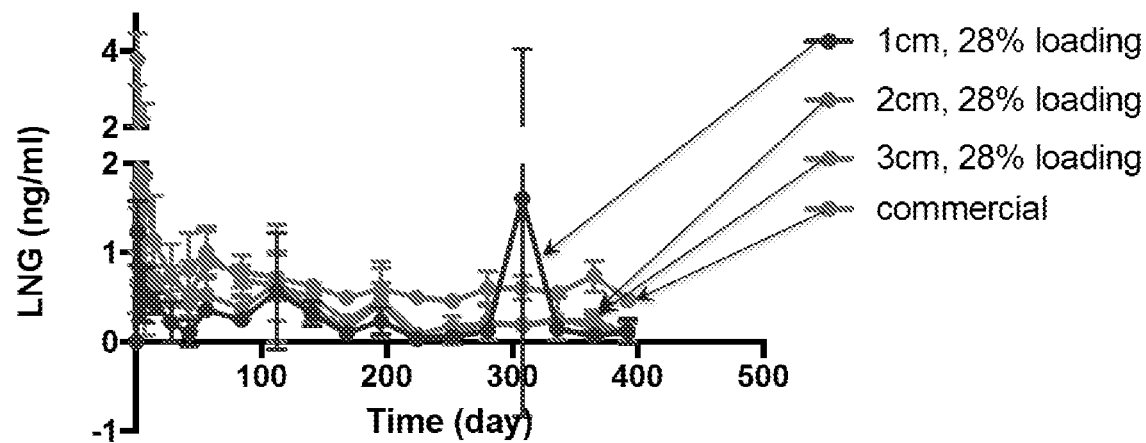
FIG. 5B shows the effect of varying implant length on LNG release (ng/ml) in rat plasma levels over time (days) after implantation.
Figure 5C:
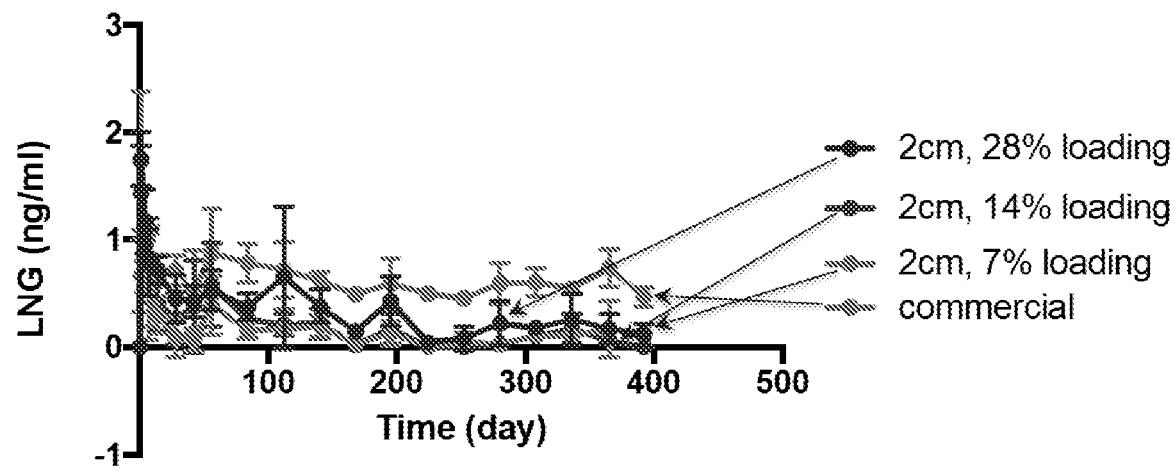
FIG. 5C shows the effect of varying drug loading percentage on LNG release (ng/ml) in rat plasma levels over time (days) after implantation.

FIGS. 5B and 5C shows the effect of varying implant length (5B) and drug loading percentage (5C) on LNG release (ng/ml) over time (days).

All of the implants of FIGS. 5A-5C were manufactured according to Method 3, except FIG. 5A, "28% (13 mg), Method 2," which was manufactured according to Method 2.

Example 5. Analysis of Implant Degradation In Vivo

Materials and Methods

Implants were removed and complete dissolved in chloroform and filtered to eliminate animal tissues. Chloroform was then evaporated in the hood. The residual solid polymer and LNG mixture was weighted. 2 ml of chloroform was added to each sample to dissolve the polymer and LNG mixture. 1 ml of the solution was taken for GPC. 20 ul of the solution is taken and diluted with ACN, filtered for HPLC.

Theoretical LNG amount before implantation is calculated using the total weight and drug loading. Implant mass after implantation is the weight of remaining material after filtering out animal tissue. LNG after implantation is measured using HPLC. Percentage of material released is the amount of material released/amount of material before implantation.

Results

The table below illustrates the results of an analysis determining the material lost from implants over time in vivo.

Figure 7:
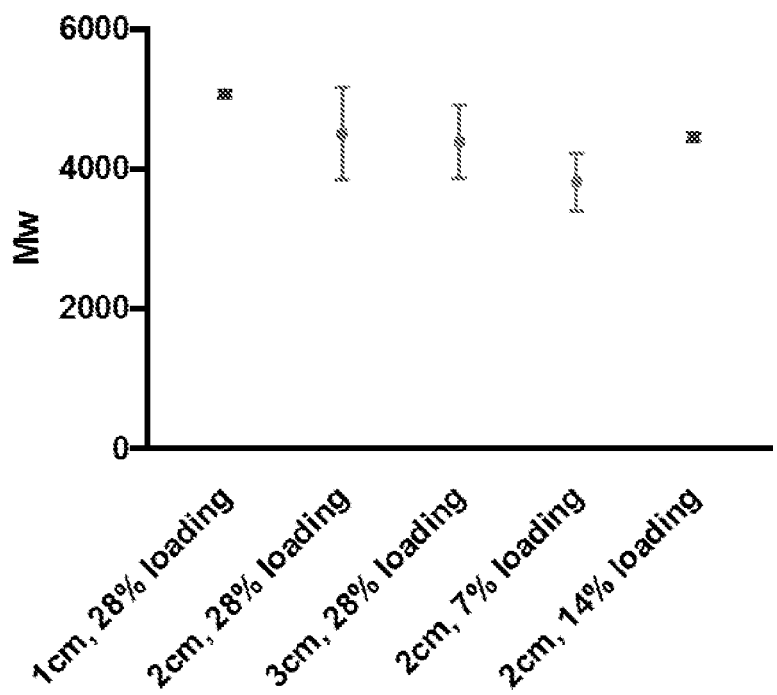
FIG. 7 is a graph showing the degradation of various implants (DO content of ~38%) after a year in vivo.

Polymer degradation is compared in FIG. 7. Compare also FIG. 7 to the in vitro results presented in FIG. 6. Polymers from the in vivo and in vitro studies had similar DO content of ~38%.

Example 6. Plasma Concentration Comparison

Blood samples were collected before implant removal (time point 0), 1 hr and 24 hr after implant removal.

Figure 8:
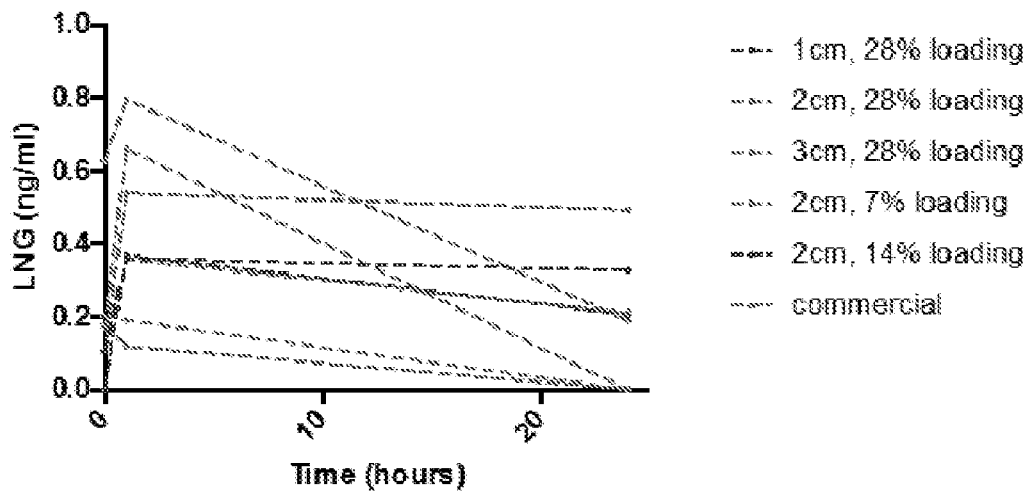
FIG. 8 is a line graph showing the plasma concentration of LNG in blood samples collected from rats before implant removal (time point 0), and at 1 hr and 24 hr after implant removal.

The results are presented in FIG. 8. SUSUK KB II® was used a commercial control.

Example 7. PDL-Co-DO Implants are Biocompatible In Vivo

Materials and Methods 30 female mice (C57/BL6), 6 months in age were utilized.

TABLE 5

Mice Utilized in Biocompatibility Study

| Group | Implant received (right/left) | Number of animal |
|---|---|---|
| Commercial Implant | None/ SUSUK KB II ® | 15 |
| PDL-co-DO | None/PDL-co-DO | 15 |

Implants were inserted into the backs of each mouse on their left side, while the right side acted as an internal control.

At months 2, 4, and 6, 5 random mice from each group were sacrificed. Tissue from the incision site was harvested and analyzed for scar tissue formation and inflammation. Implants were additionally analyzed for collagenous capsule formation.

Results

Figure 9:
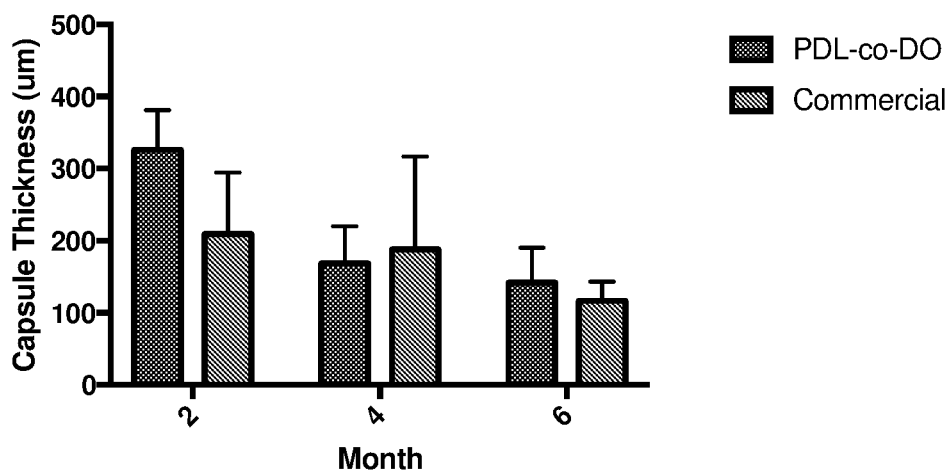
FIG. 9 is a bar graph showing the result of analysis determining the encapsulation thickness around implanted PLD-co-DO and commercial implants.

The results of the assay are illustrated in FIG. 9. The difference between encapsulation thickness of PDL-co-DO implants and commercial implants was not statistically significant.

Example 8. Implants can be Sterilized by Irradiation

Materials and Methods

A cesium irradiator capable of 566 Gy/hr was utilized. 5, 1 cm implants were fabricated. 4 implants were loaded into the cesium irradiator and retrieved one at 2, 10, 20, and 26

TABLE 4

Analysis of Material Lost from Implants In vivo

| | | 1 cm, 28% loading | | 2 cm, 28% loading | | 3 cm, 28% loading | | 2 cm, 7% loading | | 2 cm, 14% loading | |
|---|---|---|---|---|---|---|---|---|---|---|---|
| Before Implantation | Measured Implant Mass (mg) | 50.0 | 52.2 | 99.7 | 93.7 | 151.6 | 150.1 | 97.3 | 93.4 | 96.8 | 96.3 |
| | Theoretical LNG (mg) | 14 | 14.62 | 27.92 | 26.24 | 42.45 | 42.03 | 6.81 | 6.54 | 13.55 | 13.48 |
| 12 Months After Implantation | Implant Mass (mg) | 39 | 40.7 | 36.9 | 65.9 | 84.6 | 81.7 | 49.7 | 49.1 | 63.1 | 60.4 |
| | LNG (mg) | 10.48 | 9.99 | 7.87 | 14.56 | 20.76 | 19.66 | 1.98 | 2.37 | 7.56 | 6.93 |
| | Calculated Polymer (mg) | 28.52 | 30.71 | 29.03 | 51.34 | 63.84 | 62.04 | 47.72 | 46.73 | 55.54 | 53.47 |
| | LNG/Total | 27% | 25% | 21% | 22% | 25% | 24% | 4% | 4.80% | 11.99% | 11.48% |
| Material Released in 12 Months | LNG Mass Lost/Fraction (mg/percentage) | 3.52/ 25% | 4.62/ 32% | 20.04/ 72% | 11.68/ 45% | 21.69/ 51% | 22.37/ 53% | 4.83/ 71% | 4.17/ 64% | 5.99/ 44% | 6.55/ 49% |
| | Polymer Mass Lost/ Fraction (mg/percentage) | 7.48/ 21% | 6.87/ 18% | 42.76/ 60% | 16.12/ 24% | 45.31/ 42% | 46.03/ 43% | 42.77/ 47% | 40.13/ 46% | 27.71/ 33% | 29.35/ 35% | hrs. with doses ranging from 1 to 15 kGy. One implant as a time zero control. Gel Permeation Chromatography (GPC) was used to measure polymer molecular weight.

TABLE 6

Time and Dose of Radiation

| Time (hr) | Dose (kGy) |
|---|---|
| 0 | 0 |
| 2 | 1.13 |
| 10 | 5.64 |
| 20 | 11.3 |
| 26 | 14.7 |

Results

Figure 10:
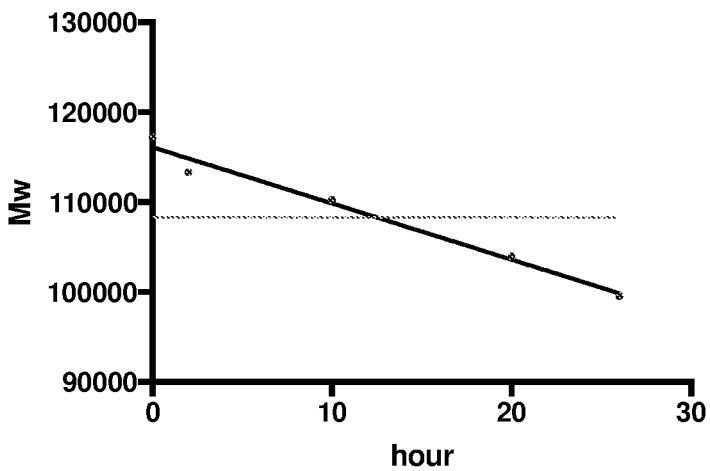
FIG. 10 is a graph showing the molecular weight of implants at various times after radiation sterilization.

Original polymer Mw after synthesis is 108,300 (FIG. 10, horizontal line).

The measured Mw from this machine is not the true Mw, rather a relative Mw to the bead standard. Changes in polymer structure (stretching out or folding in) can change the relative Mw (FIG. 10).

Nonetheless, the results show that polymer Mw has minimum change after 26 hours of irradiation.

Yellowing was observed on both the implant and the falcon tube after radiation. Yellowing was proportional to the radiation dose. Yellowing decreased over time following removal from the irradiator.

Example 8. Fabrication of Coated Implants, Core Implants, and Coated+Core Implants In addition to standard implants, coated implants, core implants, and coated+core implants are provided. Exemplary embodiments are illustrated in FIG. 11.

Pure polymer cores can be prepared by loading polymer inside a baking mold (e.g., (d=1 mm)) and baking to create pure polymer core.

Coated Implants have been prepared.

1. Polymer sheet fabrication:
Dissolve PDL-co-DO in Chloroform
Pour the solution into glass Petri dish, allow chloroform to evaporate over night at room temperature
Harvest PDL-co-DO sheet 2. Coating polymer sheets onto implants:
Implant is sandwiched between two polymer sheets and placed inside baking mold and allowed to bake for 10 min at 70-80° C. in atmosphere pressure with argon protection.

Polymer sheets with 10% and 20% PDL-co-DO: Chloroform (w/v) solution were prepared, and both yield good polymer sheets.

Polymer+LNG sheets have also been fabricated.
PDL-co-DO (DO contenet:36%) was used to test polymer +LNG sheet solvent casting conditions.
LNG loading is kept constant at 20%.
Polymer and LNG are dissolved in DCM and casted on a glass beaker.

Two mold systems were created using a Teflon block and glass slide: one without an aluminum foil layer, and one with an aluminum foil layer.

Polymer and drug mixture is loaded in the mold, compressed and baked for 1 h at 90-100 C, then compressed and cooled down. Both molds resulted in a uniform sheet. The sheet sticks on the surface of Teflon and aluminum foil. The sheet on the aluminum foil is easy to peel off from aluminum foil. Polymer and LNG sheet made with aluminum foil mold was analyzed using SEM.

An exemplary device for preparing implant coatings is illustrated in FIGS. 13A-15C.

Example 9. In Vitro Drug Release Studies with Coated Implants

Materials and Methods

Polymer sheets (also referred to as films) with 10% and 20% PDL-co-DO were coated onto LNG implants as discussed above. The films were formed by solvent evaporation from solutions of solvent/polymer that were 10% or 20% polymer. This refers to PDL-co-DO dissolved in organic solvent. 10 and 20% refers to a weight by volume. See, e.g., Example 8, 2. Coating polymer sheets onto implants. The higher the % of polymer, the thicker the film. It is believed that the thickness of the 10% coating was about 300 micron, while the thickness of the 20% coating was about 500 micron to about 600 micron.

In vitro drug release was monitored as discussed above, in comparison to a commercial control (SINO-IMPLANT (II) ®).

Results

Figure 12:
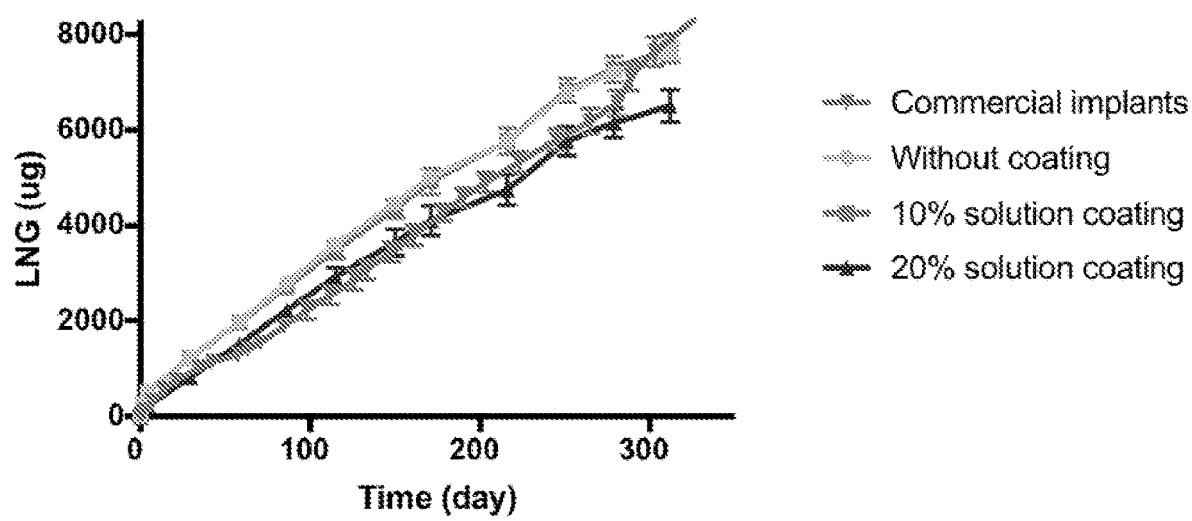
FIG. 12 is a line graph showing in vitro release of LNG (ng) from standard implants coated with 10% or 20% drug-free PLD-co-DO (e.g., coated implants) compared to a commercial implant.
Figure 13A:
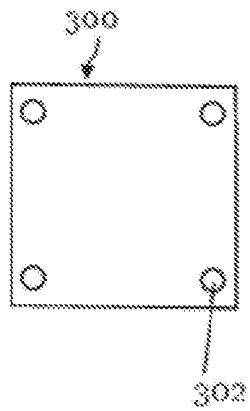
FIGS. 13A-13C show the bottom view, top view, and side view (respectively) of an exemplary mold base (300) of an exemplary sheet mold compressor system.
Figure 13B:
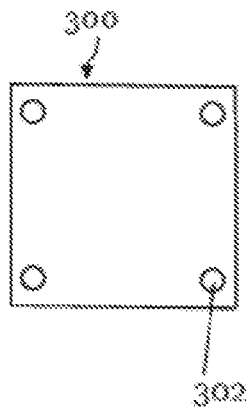
Figure 13C:
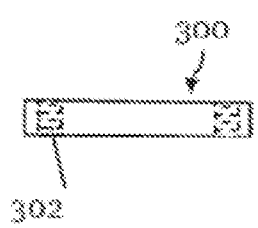
Figure 14A:
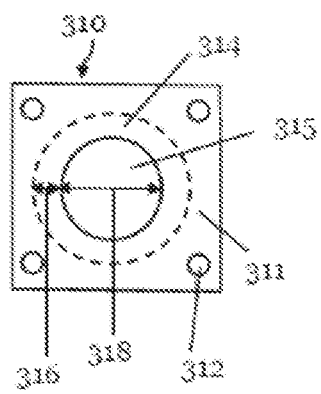
FIGS. 14A-14C show the bottom view, top view, and side view (respectively) of an exemplary shaping mold (310) of an exemplary sheet mold compressor system.
Figure 14B:
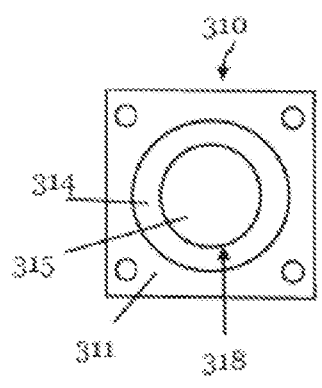
Figure 14C:
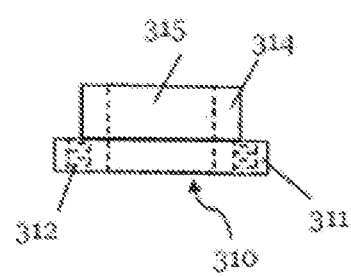
Figure 15A:
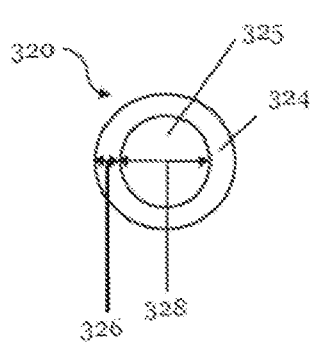
FIGS. 15A-15C show the bottom view, top view, and side view (respectively) of an exemplary compressor (320) of an exemplary sheet mold compressor system.
Figure 15B:
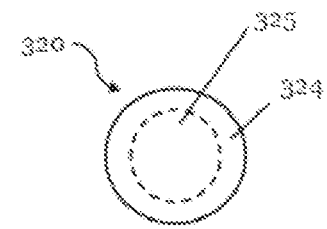
Figure 15C:
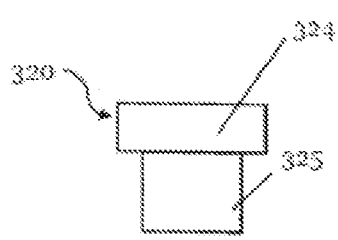

The results are illustrated in FIG. 12. Zero order release kinetics are observed for all implants. The addition of 10 and 20% coatings reduces a linear rate of release is observed for all implants. The addition of a 10 and 20% coatings (w/v), reduces release rates, while maintaining zero order release kinetics. Importantly, 20% coatings (w/v) reduce releases rates more than 10% (w/v) coatings. A burst release of LNG from commercial implants at 300 days was observed, with no burst observed in implants made by PDL-co-DO, with and without coatings.

In sum, the results illustrate that the burst release is eliminated by the coating formed with 20% polymer (i.e., the thickness of the 20% film was sufficient to eliminate the burst release), while 10% reduced, but did not eliminate the burst release. The thickness of the 20% film is believed to be several hundred microns.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A non-injectable biodegradable contraceptive implant for implantation in tissue in a female subject comprising
a contraceptive agent free biodegradable core having a coating thereon, the coating being formed of a biocompatible polyester copolymer,
wherein the biodegradable polyester copolymer is poly (ω-pentadecalactone-co-p-dioxanone) having a general structure according to Formula (I)

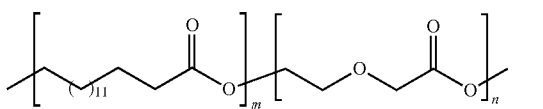

Formula (I)

wherein n and m are independently integer values of less than or equal to about 1500, and having in the coating on the core, but not in the core, an effective amount of a contraceptive agent being released with zero order kinetics to prevent pregnancy in the female subject over a period of twelve to twenty-four months, and an outer biodegradable poly(ω-pentadecalactone-co-p-dioxanone) coating on the coating on the core, wherein the outer coating does not contain contraceptive agent.

2. The implant of claim 1, wherein the poly(o- pentadecalactone-co-p-dioxanone) has a dioxanone (DO) mol % content in the range of about 20 to about 60% forming the outer coating and the coating on the core.

3. The implant of claim 2, wherein the contraceptive agent is selected from the group consisting of estrogen, progestogen agents or progesterone receptor modulators.

4. The implant of claim 3 wherein the contraceptive agents is selected from the group consisting of progesterone, 17-hydroxy progesterone, norethindrone acetate, ethynodiol esters, 19-nor-17-hydroxy progesterone esters, 17-alpha-ethinyltestosterone, 17- alpha-ethinyl-19-nor-testosterone and derivatives thereof, norethindrone diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgesterol, DL-norgestrel, D-17-alpha-acetoxy-13-beta-ethyl-17-alpha-ethinyl-gon- 4-en-3-one oxime, gestodene, desogestrel, DMPA-depo medroxyprogesterone acetate, norgestimate, nestorone, drospirenone, ulipristal acetate, mifepristone, CDB-4124, active salts or metabolites thereof, and mixtures thereof.

5. The implant of claim 3, wherein the implant comprises about 20 to about 60 mg of levonorgestrel.

6. The implant of claim 1, wherein the implant is suitable for subcutaneous implantation.

7. The implant of claim 1, wherein the copolymer forming the coating on the core and the outer coating degrades after release of the contraceptive agent.

8. The implant of claim 1 in the form of a rod, cylinder, bead, film, or disk.

9. The implant of claim 1 having a percent contraceptive agent loading from about 1% to about 80% of the copolymer in the coating on the core or a weight ratio of copolymer in the coating on the core to contraceptive agent of about 3:1, 2.5:1, 2:1, or 1:1.

10. The implant of claim 1 further comprising additional therapeutic, prophylactic or diagnostic agents other than the contraceptive agent.

11. The implant of claim 1 wherein the contraceptive agent in the coating on the core is in a loading between about 5% and about 30%.

12. The implant of claim 11, wherein the coatings comprise a copolymer having a % DO of between 39 and 50%.

13. A method of using the implant of claim 1, comprising implanting the implant subcutaneously in a subject in need thereof.

14. The method of claim 13, wherein the contraceptive agent is released over a period of 12 to 24 months.

15. The implant of claim 9 having a percent contraceptive agent loading from about 1% to about 50% by weight of the copolymer forming the coating on the core.

16. The implant of claim 1 wherein the thickness of the outer coating or coating on the core core is effective to reduce release from the implant.

17. The implant of claim 1 wherein the core is formed of a biodegradable polymer.

* * * * *